US00PP28250P3

(12) United States Plant Patent
Dai et al.

(10) Patent No.: US PP28,250 P3
(45) Date of Patent: Aug. 8, 2017

(54) STRAWBERRY PLANT NAMED 'YASMIN'

(50) Latin Name: *Fragaria×ananassa Duch. (Fragaria L.)*
Varietal Denomination: YASMIN

(71) Applicant: State of Israel, Bet Dagan (IL)

(72) Inventors: Nir Dai, Kfar Maas (IL); Zecharia Tanami, Hasmonaim (IL); Sara Slotzky, Or Yehuda (IL); Ahuva Daos, Mazkeret Batia (IL)

(73) Assignee: State of Israel, Ministry of Agriculture & Rural Development, Agriculture Research Organization, Bet Dagan (IL)

( * ) Notice: Subject to any disclaimer, the term of this patent is extended or adjusted under 35 U.S.C. 154(b) by 42 days.

(21) Appl. No.: 14/545,407

(22) Filed: May 1, 2015

(65) Prior Publication Data

US 2016/0324051 P1 Nov. 3, 2016

(51) Int. Cl.
*A01H 5/08* (2006.01)

(52) U.S. Cl.
USPC ..... Plt./209

(58) Field of Classification Search
USPC ..... Plt./209
See application file for complete search history.

(56) References Cited

PUBLICATIONS

UPOV hit on a strawberry plant named 'Yasmin', IL PBR 3307, granted Feb. 25, 2014.*
Printout of application information from PLUTO database for corresponding Israel Plant Breeders' Rights application No. 4298 filed Oct. 12, 2010 (1 page) (retrieved from www.wipo.int/pluto).

* cited by examiner

*Primary Examiner* — Anne Grunberg
(74) *Attorney, Agent, or Firm* — Foley & Lardner LLP

(57) ABSTRACT

A new and distinct *Fragaria ananassa* plant named 'YASMIN', particularly characterized by very early flowering, compact growth habit, and short-conical fruit shape.

6 Drawing Sheets

Figure 1:
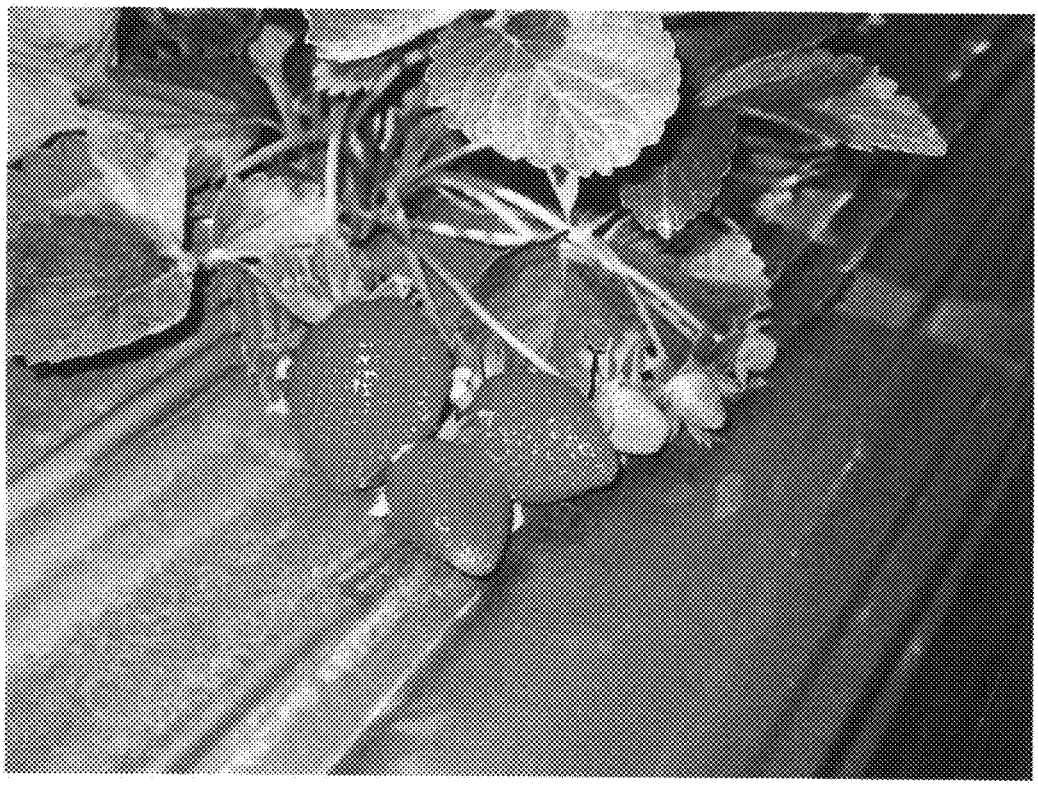

Botanical name of the genus and species of the plant claimed: *Fragaria×ananassa* Duch. (*Fragaria* L.)
Variety denomination: 'YASMIN'.

BACKGROUND OF THE INVENTION

The present invention relates to a new and distinct variety of a strawberry plant, botanically known as *Fragaria× ananassa* Duch. (*Fragaria* L.) of the Rosaceae family, and hereinafter referred to by the variety denomination 'YASMIN'.

The new *Fragaria ananassa* variety is a product of a planned breeding program conducted by the inventors, Nir DAI, Zecharia TANAMI, Sara SLOTZKY and Ahuva DAOUS, in The Volcani Center, located in Bet Dagan, Israel. The objective of the breeding program was to develop a new *Fragaria ananassa* variety with early season high fruit production, which starts in the beginning of November under conditions prevailing in Israel.

The new *Fragaria ananassa* variety originated from a cross made by the inventors in 2005, in a controlled greenhouse in The Volcani Center, Bet Dagan, Israel. The female or seed parent is the *Fragaria ananassa* proprietary breeding line designated 'ARO 105' (unpatented). The male or pollen parent is the *Fragaria ananassa* proprietary breeding line designated 'ARO 701' (unpatented). The new *Fragaria ananassa* 'YASMIN' was observed and selected by the inventors within the progeny of the stated cross in a controlled environment in 2007 in The Volcani Center, Bet Dagan, Israel.

Asexual propagation of the new *Fragaria ananassa* variety by stolons was first performed in June 2007 in The Volcani Center, Bet Dagan, Israel, and has demonstrated that the combination of characteristics as herein disclosed for the new variety was firmly fixed and retained through successive generations of asexual propagation. The new variety propagates true-to-type.

BRIEF DESCRIPTION OF THE INVENTION

The following traits have been repeatedly observed and are determined to be characteristics of 'YASMIN', which in combination, distinguish this strawberry plant as a new, unique and distinct variety:

1. Very early beginning of flowering which is in the first week of October, in Israel;
2. Compact growth habit;
3. Short-conical fruit shape.

In comparison to the parental varieties, 'ARO 105' and 'ARO 701', 'YASMIN' differs primarily in the traits listed in Table 1.

TABLE 1

Comparison with parent varieties.

| Trait | New Variety 'YASMIN' | Female Parent 'ARO 105' (unpatented) | Male Parent 'ARO 701' (unpatented) |
|---|---|---|---|
| Fruit length | short | long | medium to long |
| Fruit color | red | light red | medium to dark red |

TABLE 1-continued

| Comparison with parent varieties. | | | |
|---|---|---|---|
| Trait | New Variety 'YASMIN' | Female Parent 'ARO 105' (unpatented) | Male Parent 'ARO 701' (unpatented) |
| Plant growth habit | compact | medium dense | medium dense |
| Inflorescence position relative to foliage | above | above | At level with |

Of the many commercial varieties known to the present inventors, the most similar in comparison to the new *Fragaria ananassa* 'YASMIN' is *Fragaria ananassa* 'TAMAR', (Patented, U.S. Plant Pat. No. 11,135) which differs from the new strawberry 'YASMIN' in the characteristics described in Table 2:

TABLE 2

| Comparison with a well known commercial variety. | | |
|---|---|---|
| Characteristic | New Variety 'YASMIN' | Comparison Variety TAMAR (U.S. Plant Pat. No. 11,135) |
| Beginning of flowering | very early | early |
| Plant growth habit | compact | Medium dense |
| Fruit shape | conical | conical |
| Sensitivity to Powdery mildew | Tolerant | Susceptible |

BRIEF DESCRIPTION OF THE PHOTOGRAPHS

The accompanying photographs illustrate the overall appearance of the new *Fragaria ananassa* variety 'YASMIN' showing the colors as true as is reasonably possible with colored reproductions of this type. Colors in the photographs may differ slightly from the color values cited in the detailed morphological description, which accurately describe the color of 'YASMIN'.

FIG. 1—Shows a typical fruit bearing plant of 'YASMIN'.

Figure 2:
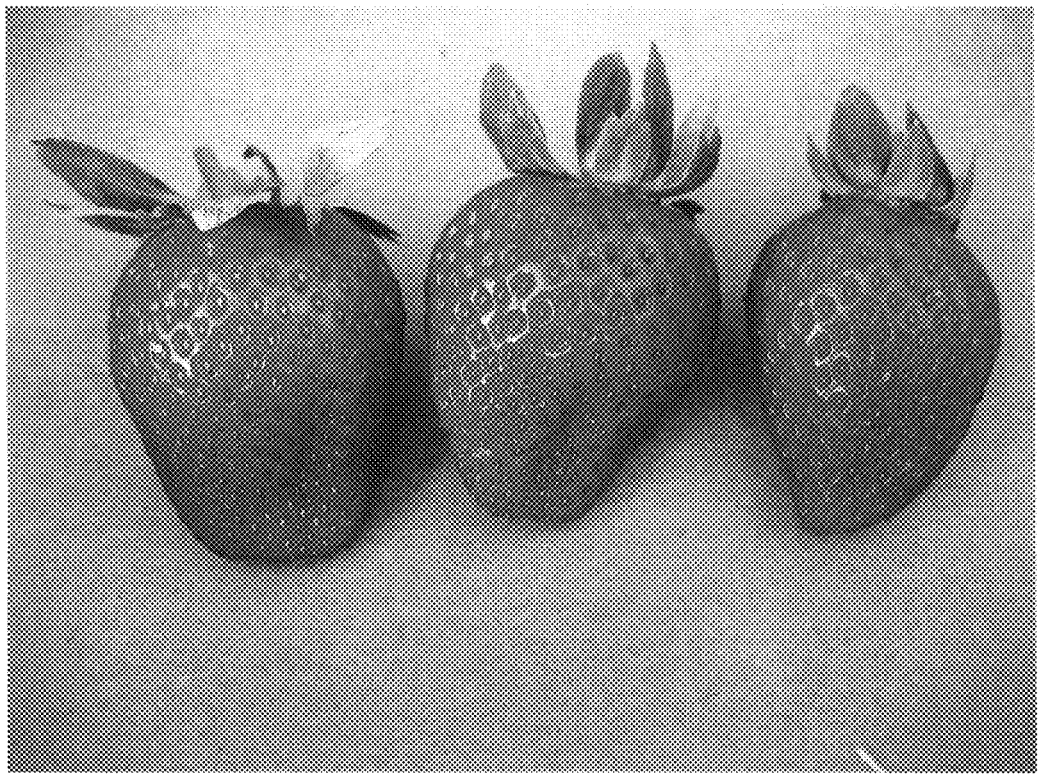

FIG. 2—Shows a typical fruit of 'YASMIN'.

Figure 3:
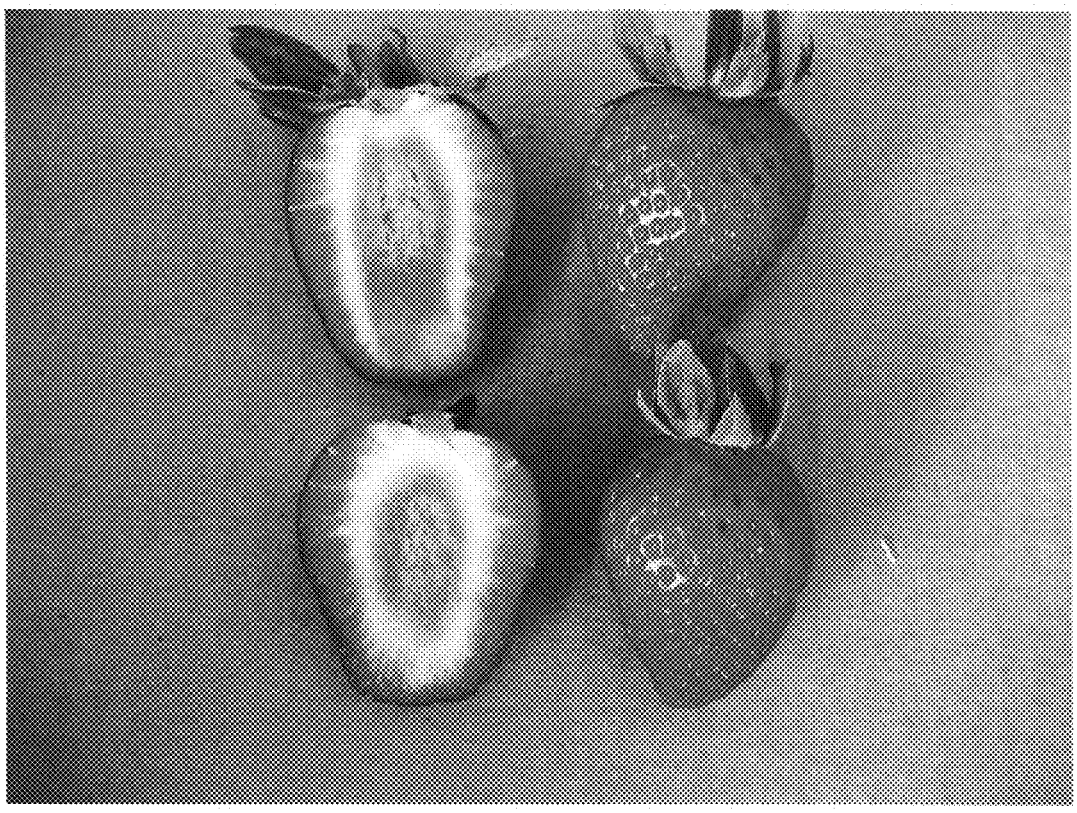

FIG. 3—Shows a typical fruit of 'YASMIN' in longitudinal section.

Figure 4:
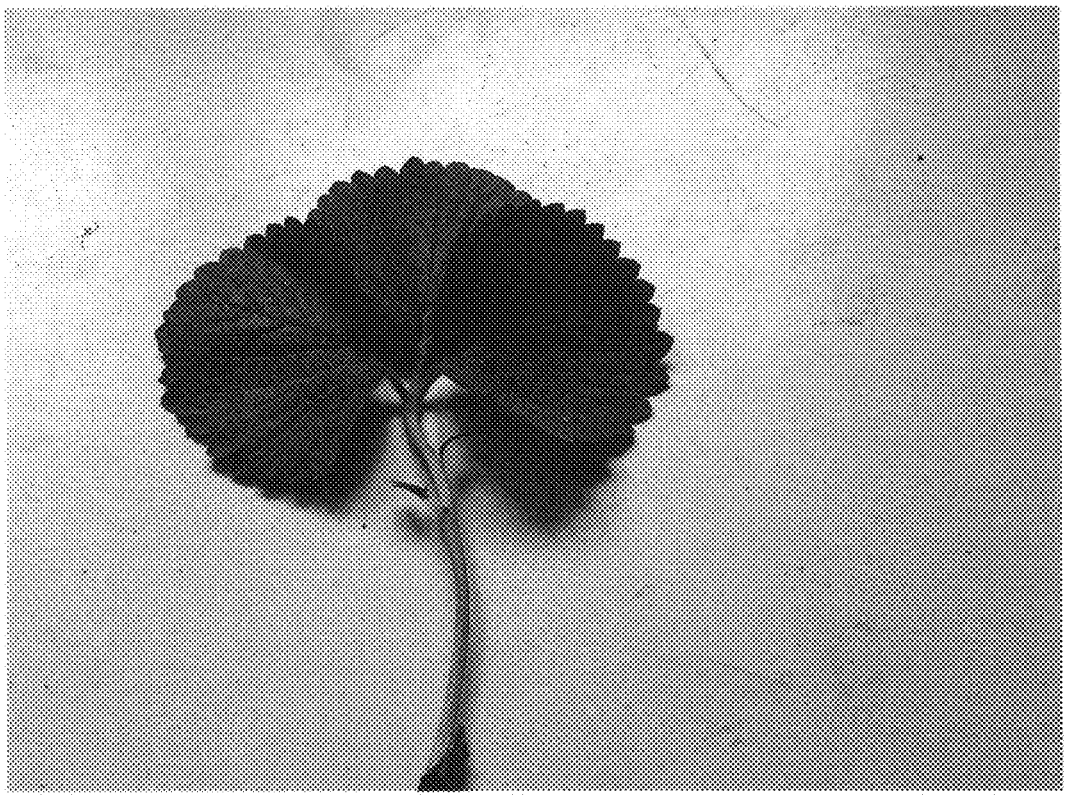

FIG. 4—Shows a typical leaf of 'YASMIN'

Figure 5:
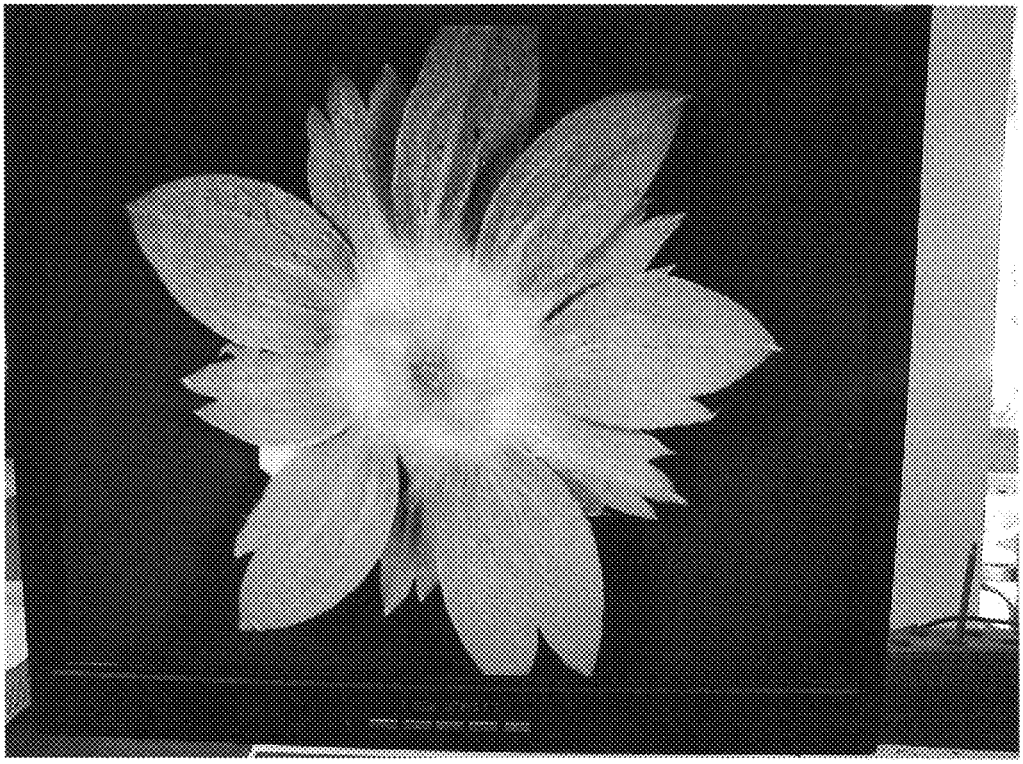

FIG. 5—Shows a typical calyx of 'YASMIN'

Figure 6:
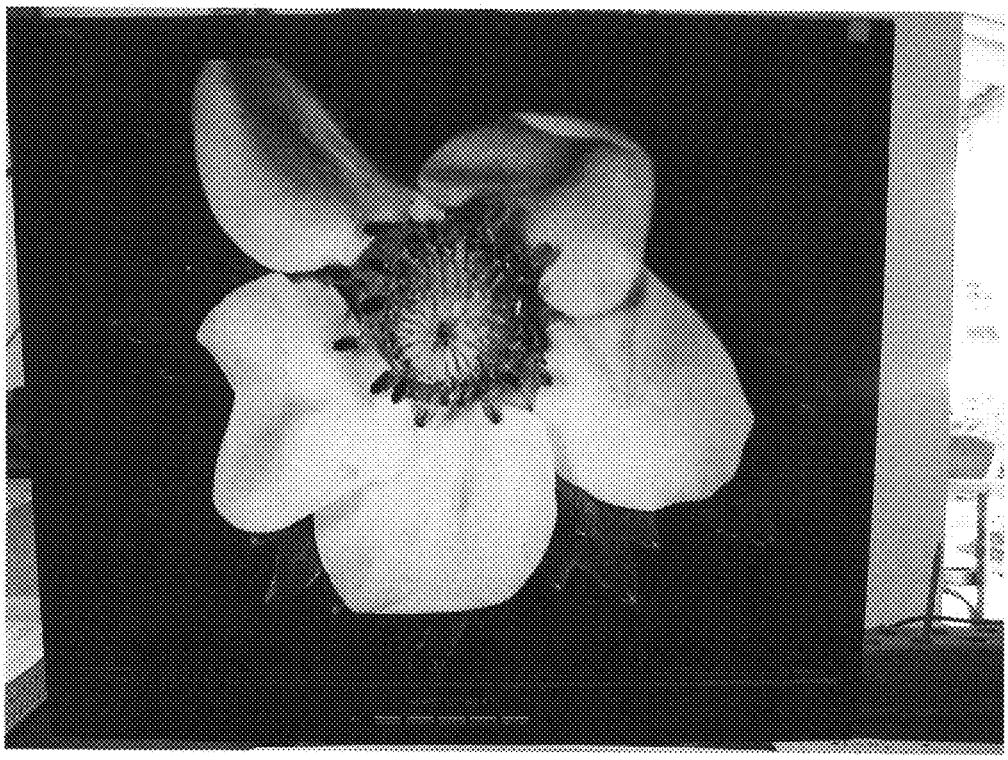

FIG. 6—Shows a typical flower of 'YASMIN'

DETAILED BOTANICAL DESCRIPTION

The new *Fragaria ananassa* 'YASMIN' has not been observed under all possible environmental conditions. The phenotype of the new variety may vary with variations in environment such as temperature, light intensity, day length or soil without any change in the genotype of the strawberry plant.

The aforementioned photographs, together with the following observations, measurements and values describe plants of 'YASMIN' as grown in the field in The Volcani Center, Bet Dagan, Israel, under conditions which closely approximate those generally used in commercial practice. The described plants were propagated from stolons and planted at a distance of 0.3×0.3 m in sandy red loam soil at an elevation of about 30 meters above sea level, with drip irrigation and fertilizers as generally used in commercial practice. Average annual rainfall is about 550 mm, with an average 350 mm of rainfall in winter (December to February). Mean diurnal minimum temperature in January is 7.2° C., and mean diurnal maximum temperature in July is 30.8° C.

Mother plants provided from an authorized nursery are planted in the beginning of May, in the field nursery at 2.5 m×2.5 m distance. Combination of overhead and drip irrigation with addition of fertilizers is used. The average day/night temperatures during the establishment of the daughter plants, between June to August, are 32° C./18° C. respectively. Runners appear from June, which produce young daughter plants up till mid September, these are then collected and planted directly in the commercial fields. Growing conditions at the fruit production field:

The bare-rooted plants are washed from soil and dipped in Octav (Prochloraz manganese) 2 g/Liter solution to avoid anthracnose. These bare rooted plants are then planted in raised beds with overhead irrigation in 4 rows at 30 cm apart. Distance between plants within rows is 32 cm. During the first month, no fertilizers are added, due to the addition of 60-100 $m^3$/hectar compost during field preparation. About 4 weeks after planting the beds are covered with silvery-black, 30 micron polyethylene. The young plants are pulled out through the pre-prepared holes. From this point on, the plants are irrigated with a drip system with a supply of additional fertilizers, as is typically used in agricultural practice. By the end of October the beds are covered with transparent, 80 micron thick polyethylene tunnels. The average day (max) and night (minimum) temperatures during the cultivation season are shown in the table below.

Unless otherwise stated, the detailed morphological description includes observations, measurements and values taken from 2012 to 2014 and based on 'YASMIN' plants grown in the nursery at The Volcani Center, Bet Dagan, Israel. Quantified measurements are expressed as an average or a range of measurements taken from a number of plants of 'YASMIN'. The measurements of any individual plant or any group of plants, of the new variety may vary from the stated average or range.

Color references are made to The Royal Horticultural Society Colour Chart (R.H.S.), (1986 edition), except where general colors of ordinary significance are used. Color values were taken under daylight conditions in full sunlight in The Volcani Center, located in Bet Dagan, Israel.

All of the plants of 'YASMIN', insofar as they have been observed, have been consistent in all the characteristics described below.

Classification:

*Botanical.*—*Fragaria ananassa*×*ananassa* Duch. (*Fragaria* L.).

Parentage:

*Female or seed parent.*—*Fragaria ananassa* 'ARO 105' (unpatented).

*Male or pollen parent.*—*Fragaria ananassa* 'ARO 701' (unpatented).

Propagation: Vegetatively from stolons.

Growing conditions:

*Light intensities.*—Full sunlight.

| | January | February | March | April | May | June | July |
|---|---|---|---|---|---|---|---|
| Mean maximum air temperature (° C.) | 17.8 | 18.1 | 20.1 | 24.5 | 27 | 29.2 | 30.8 |
| Mean minimum air temperature (° C.) | 7.2 | 7.1 | 8.8 | 11.5 | 14.6 | 17.9 | 20.6 |
| Mean rainfall (mm) | 140.5 | 96.9 | 66.1 | 17.5 | 2.2 | — | — |

| | August | September | October | November | December |
|---|---|---|---|---|---|
| Mean maximum air temperature (° C.) | 31.2 | 30.4 | 28.3 | 24.1 | 19.7 |
| Mean minimum air temperature (° C.) | 21.2 | 19.4 | 16 | 11.8 | 8.6 |
| Mean rainfall (mm) | — | 0.4 | 20.4 | 76.2 | 130.3 |

*Fertilization.*—A balanced fertilizer with level of 3-1-9 (N-P-K)+3% microelements.

*Growth regulators.*—Not applied.

TABLE OF CHARACTERISTICS

Plant

Habit: round, compact
Height: 25-30 cm.
Diameter: 25-30 cm.
Density: medium.
Vigor: strong.

Leaf

Color of upper side: medium to dark green RHS 137 B.
Color of lower side: medium green RHS 138 B.
Length: 8-12 cm.
Width: 10-14 cm.
Cross section: slightly concave.
Blistering: medium strong.
Number of leaflets: more than 3.
Glossiness: None

Terminal leaflet

Length: 60-65 mm.
Width: 55-65 mm.
Shape of base: obtuse.
Shape of teeth: rounded.

Side leaflet

Length: 55-60 m.
Width: 65-70 mm.
Shape of base: truncate.

Petiole

Pose of hairs: outwards.
Length: 9-13 cm.
Thickness: about 3 mm.
Green color: light green RHS 144 C.
Anthocyanin coloration: absent.

Stipule

Length: 25-30 mm.
Width: 6-9 mm.
Anthocyanin coloration: absent.
Color: very light green RHS 144 D.

-continued

TABLE OF CHARACTERISTICS

Stolons

Number: numerous.
Anthocyanin coloration: weak.
Thickness: 2-3 mm.
Pubescence: medium outwards.

Inflorescence

Position relative to foliage: above.
Attitude: erect.
Peduncle length: 7 to 18 cm

Flower

Number of flowers per plant: numerous
Diameter: 25-33 mm.
Size of calyx relative to corolla: 33-40 mm.
Size of inner calyx relative to outer calyx: smaller.
Spacing of petals: strongly overlapping.
Number of petals per flower: 6 to 8
Length of sepal: 17-23 mm.
Width of sepal: 9-12 mm.
Color of sepal: medium green RHS 137 D.
Number of sepals per flower: 11 to 14

Petal

Length: 13-15 mm.
Width: 14-15 mm.
Shape: rounded.
Color of upper side: white RHS 155 B.
Color of lower side: white RHS 155 B.

Stamen

Number per flower: about 20
Color: Yellow green RHS 150 A

Filament:

Length: 2-3 mm
Color: Very light green RHS 145 D

Fruiting truss

Attitude: prostrate.
Thickness: about 2 mm.
Color: light green RHS 144 B.
Pubescence: strong.
Number of fruit per truss: 1 to 3

Fruit

Difference in shapes between primary and secondary fruits: clear.

Fruit of primary order

Length: 37-45 mm.
Maximum diameter: 32-39 mm.
Weight: about 25 g.
Predominant shape: wedged.
Band without achenes: 3-6 mm.
Unevenness of surface: smooth.
Color: very dark red RHS 42 A.
Evenness of color: rather even.
Glossiness: medium to strong.
Insertion of achenes: sunken.
Insertion of calyx: at level.
Color of achenes: light green RHS 145 A
Density of achenes: medium dense.
Number of achenes: 300-450.
Pose of the calyx segments: reflexed.
Size of calyx in relation to fruit diameter: similar.
Length of outer calyx segment: 20-25 mm.
Width of outer calyx segment: 10-12 mm.
Color of inner calyx segment: medium to dark green RHS 137 B.
Color of outer calyx segment : medium green RHS 137 D.
Adherence of calyx: very strong.
Firmness: firm.

-continued

| TABLE OF CHARACTERISTICS | |
|---|---|
| | Color of flesh: medium to dark red RHS 42 D and white RHS 155 B.<br>Evenness of color of flesh: uneven.<br>Sweetness: good sweetness, Brix 8.0-9.5%.<br>Acidity: Medium to low acidity pH 3.75 -3.9. |
| Fruit of secondary order (representative) | |
| | Length: about 45 mm.<br>Maximum diameter: about 35 mm.<br>Weight: 20-25 g.<br>Predominant shape: conical.<br>Band without achenes: 3-6 mm.<br>Unevenness of surface: smooth.<br>Color: very dark red RHS 42 A.<br>Evenness of color: rather even.<br>Glossiness: medium to strong.<br>Insertion of achenes: sunken.<br>Insertion of calyx: at level.<br>Color of achenes: light green RHS 145 A<br>Density of achenes: medium dense.<br>Number of achenes: 300-450.<br>Pose of the calyx segments: reflexed.<br>Size of calyx in relation to fruit diameter: similar.<br>Length of outer calyx segment: 20-25 mm.<br>Width of outer calyx segment: 10-12 mm. |

-continued

| TABLE OF CHARACTERISTICS | |
|---|---|
| | Color of inner calyx segment : medium to dark green RHS 137 B.<br>Color of outer calyx segment : medium green RHS 137D.<br>Adherence of calyx: very strong.<br>Firmness: firm.<br>Color of flesh: medium to dark red RHS 42 D and white RHS 155 B.<br>Evenness of color of flesh: uneven.<br>Sweetness: good sweetness, Brix 8.0-9.5%.<br>Acidity: Medium to low acidity pH 3.75-3.9.<br>Fruit cavity size: 1-3 mm |
| Time of flowering | Very early (in early plantings around October 10th) |
| Time of ripening | Early (start at 10th of November) |
| Type of bearing | Remontant |

*Maturity*.—Ripe for commercial harvesting on about November 10$^{th}$ is Israel.

Disease resistance: Tolerant to Powdery mildew.

Pest resistance: No atypical resistance has been noted.

Disease susceptibility: None observed.

Pest susceptibility: Susceptible to red spider mites.

What is claimed is:

1. A new and distinct variety of *Fragaria ananassa* plant named 'YASMIN', as illustrated and described herein.

* * * * *